United States Patent [19]

Seibert et al.

[11] Patent Number: 5,450,358
[45] Date of Patent: Sep. 12, 1995

[54] METHOD AND SYSTEM FOR MONITORING THE QUALITY OF A WATER PURIFICATION APPARATUS

[75] Inventors: N. Michael Seibert, Los Angeles; Hilton L. Stonerock, Saugus, both of Calif.

[73] Assignee: McKesson Corporation, San Francisco, Calif.

[21] Appl. No.: 275,670

[22] Filed: Jul. 15, 1994

Related U.S. Application Data

[63] Continuation of Ser. No. 768,808, Sep. 30, 1991, abandoned.

[51] Int. Cl.$^6$ ............................................. G01R 23/16
[52] U.S. Cl. ..................... 364/497; 364/502; 364/551.01; 324/694
[58] Field of Search ............... 340/603; 210/85, 87; 324/446, 439, 694-706, 709, 442; 364/496, 497, 500, 502-509, 510, 550, 551.01

[56] References Cited

U.S. PATENT DOCUMENTS

| | | | |
|---|---|---|---|
| Re. 31,750 | 11/1984 | Morrow | 364/550 X |
| 3,990,066 | 11/1976 | Malmgren | 340/603 |
| 4,469,602 | 9/1984 | Seal | 364/502 X |
| 4,806,912 | 2/1989 | Clack | 340/603 |
| 4,833,622 | 5/1989 | Barto et al. | 364/496 |
| 4,851,818 | 7/1989 | Brown et al. | 210/85 X |
| 4,881,176 | 11/1989 | Kononov | 364/502 X |
| 4,937,557 | 6/1990 | Tucci et al. | 340/603 |
| 4,967,381 | 10/1990 | Lane et al. | 364/551.01 |
| 5,057,212 | 10/1991 | Burrows | 210/85 |
| 5,145,575 | 9/1992 | Burrows | 210/85 |

*Primary Examiner*—Emanuel T. Voeltz
*Assistant Examiner*—Craig Steven Miller
*Attorney, Agent, or Firm*—Flehr, Hohbach, Test, Albritton & Herbert

[57] ABSTRACT

A water quality monitoring system (30) assessing the performance of a water purification apparatus (10) which compares the current percentage differential ion concentration or rejection ratio ($R_x$), between the upstream inlet (12) and downstream outlet (14) of the purification apparatus (10), with a previous sequence of rejection ratios ($R_1, \ldots R_n$) to determine the true performance of the water purification apparatus (10). Each $R_x$ value is determined at a different selected time for use in conjunction with a computation device (40) interconnected between a comparator device (38), calculating $R_x$, and a storage mechanism (42), storing the sequence of ($R_1, \ldots R_n$) values. The computation device (40) computes a performance value (PV) which is an indication of the filter membrane performance. This performance value is calculated according to a predetermined formula which incorporates the rejection ratios ($R_1, \ldots R_n$) as variables. The method of monitoring the quality of water comprises the steps of determining a specific rejection ratio ($R_x$) in the ion concentration between the upstream water supply (12) and the downstream product water output (14) at a selected time. The next step includes calculating a Performance Value PV by the computation device (40) according to the predetermined equation by incorporating a sequence of rejection ratios ($R_1, \ldots R_n$). Finally, comparing the PV to a predetermined range of values corresponding to a calibrated scale in order to evaluate the overall performance of the water purification apparatus (10).

17 Claims, 1 Drawing Sheet

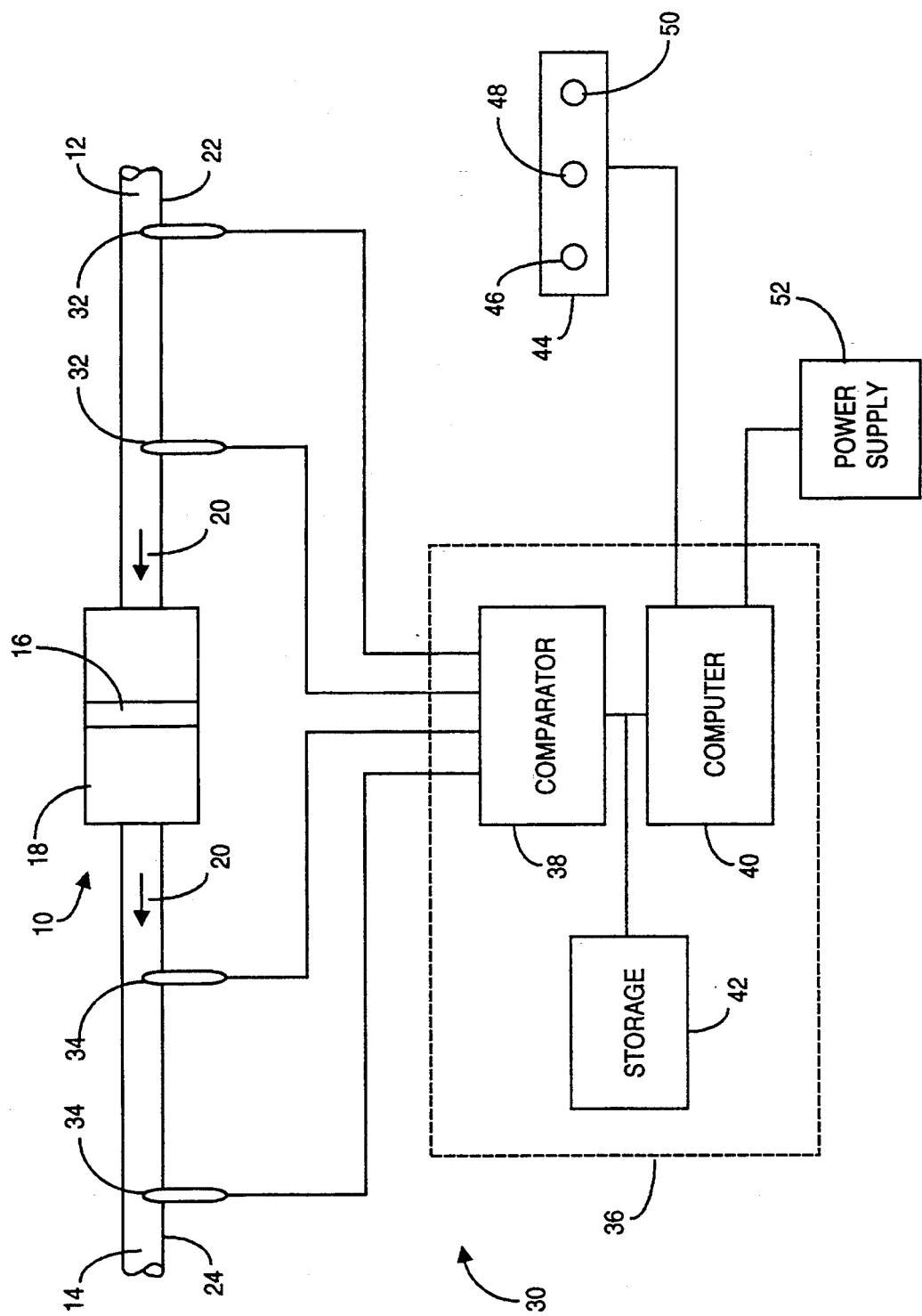

METHOD AND SYSTEM FOR MONITORING THE QUALITY OF A WATER PURIFICATION APPARATUS

This is a continuation of application Ser. No. 07/768,808 filed Sep. 30, 1991 now abandoned.

BACKGROUND OF THE INVENTION

1. Field of the Invention

The present invention relates, generally, to water quality monitors and, more particularly, to quality monitors for reverse osmosis water purification apparatuses.

2. Description of the Related Art

As the public becomes more aware of the potential environmental and health hazards associated with our municipal water supply sources, water purification apparatuses have experienced an increase in commercial and residential use. In many rural areas, the water source supplied to homes and industries may originate from wells, reservoirs through underground pipes or other sources. Often these water supplies contain a high levels of dissolved minerals, agricultural nutrients, and even health hazardous chemicals such as insecticides. Thus, many of those conscious of their drinking and bathing water have installed water purification apparatuses between the inlet water source and the product water in an attempt to remove these undesirable substances. In particular, reverse osmosis water purification apparatuses are more commonly used for removing ionic substances dissolved in the supply water.

Typically, the reverse osmosis water purification apparatus includes a housing having a removable semipermeable membrane positioned therein which separates the feed water from the product water. These membranes exhibit a propensity for equalizing the concentration of metallic ions dissolved in the water on opposed sides of the membrane. Due to the imbalance of ion concentration, a pressure, commonly known as the osmotic pressure, forces the water through the membrane from the side of lesser ion concentration to the side of greater concentration. Only until concentration equilibrium does the osmotic pressure subside.

This process may be reversed by increasing the fluid pressure on the side of the membrane exhibiting the greater metallic ion concentration which causes the water to flow in the reverse direction; hence the term "reverse osmotic pressure". During this process, the membrane essentially functions as a filter for separating the dissolved substances from the water in which they are suspended.

Under ideal conditions, a reverse osmosis system will filter or reject approximately 95% of the dissolved salts, ferrous particles or other common ions. A rejection ratio of around 70%, however, is acceptable for most applications. Over a period of use or time, the membrane becomes less effective and more susceptible to failure. Often the membrane becomes saturated with contaminants, precipitates, scale, or particulate matter on the water source side of the membrane. Thus, in order for the reverse osmosis water purification apparatus to function properly and efficiently, it is desirable to replace the membrane or service the system when the rejection ratio consistently falls below the acceptable range (i.e., 70%).

Accordingly, it is desirable to monitor the performance of the membrane in order to warn the user when replacement is necessary. One common method of determining membrane performance is to measure the Parts Per Million (PPM) level of dissolved solids in each fluid body (i.e., upstream and downstream) and then calculating the ratio therebetween to determine the percentage difference in ion concentration. Because the concentration of ions in each fluid body is inversely proportional to the resistance of the water, the ion content can easily be calculated by measuring this resistance. Typical monitoring techniques include electronically coupling two electrodes together and passing a current therebetween to measure the resistance, and hence, the PPM concentration.

One problem associated with this technique is that the conductivity or resistivity of the water has been found to be a function of the water temperature. When the water temperature increases, the conductivity increases, while the resistivity decreases. Thus, the resistivity readings vary as the temperature varies. Numerous water quality monitoring devices incorporating this technique of measuring the resistance in the upstream inlet source and the downstream outlet source, have attempted to overcome these conductivity or resistivity variations by introducing various arrays of electronics between the pairs of electrodes.

Typical of such an approach is the monitoring systems disclosed in U.S. Pat. Nos. 4,937,557 to Tucci et al. and to 3,838,774 to Dolan et al. Both devices couple the downstream electrodes to the input resistance of an operational amplifier while coupling the upstream electrodes to the negative feedback loop of the operational amplifier. Because the gain of the operational amplifier is proportional to the ratio between the feedback resistance and the input resistance, this gain represents a continuous measurement of the relative impurity level. This measurement should remain constant during resistance variations. Henceforth, both provide circuitry which compares the gain to a predetermined level; energizing an alarm should the ratio fall below the predetermined level. Although these devices have been adequate to compensate for the resistance variations due to the water temperature changes, they, generally, do not account for the environmental variations which affect the reverse osmosis membrane itself.

The filtering capacity of the membrane has been found to fluctuate due to vacillations in the ion content of the supply water. More importantly, the membranes themselves are sensitive to changes in water temperature, as well as water pressure, even though the membrane may be functioning properly. For example, a substantial temperature increase in the water (not uncommon during the summertime) will increase the capillary size in the semi-permeable membrane leading to an increase in the passage of larger ions. Similarly, a city water pressure decrease, occurring during periods of excessive city use, also results in an increase in capillary size in the membrane. Moreover, these conditions are compounded during the summertime where water usage is generally higher. Thus, these temporary adverse conditions may inconvenience the user by falsely indicating that the semi-permeable membrane's performance has been reduced. Other prior art water quality monitoring apparatus which use the resistance method of measuring the PPM in each fluid body are disclosed in U.S. Pat. Nos. 4,851,818; 4,849,098; 4,806,912; 4,623,451 and 3,990,066.

Although the water quality monitoring systems noted above assess the present performance, adjusting for change in resistivity of the water due to temperature variations, they do not take into account the above-mentioned temporary adverse conditions which may affect the membrane performance itself.

Accordingly, it is an object of the; present invention to provide a water quality monitoring system and method which is improved and more reliable.

It is a further object of the present invention to provide a water quality monitoring system and method which discounts temporary adverse environmental conditions affecting reverse osmosis membrane performance.

Still another object of the present invention is to provide a water quality monitoring system and method which informs the users of the true condition of the membrane and alerts them that replacement is necessary.

Yet, it is another object of the present invention to provide a water quality monitoring system and method which minimizes power consumption and reduces plating or build up of deposits on the electrodes.

Another object of the present invention is to provide a water quality monitoring system and method which can be easily retrofit to existing reverse osmosis water purification apparatuses.

It is a further object of the present invention to provide a water quality monitoring system and method which is durable, compact, easy to maintain, has a minimum number of components, is easy to use, and is economical to manufacture.

The apparatus of the present invention has other objects and features of advantage which will be more readily apparent from the following description of the best mode of carrying out the invention and the appended claims, when taken in conjunction with the accompanying drawing.

Accordingly, there has been a need for a water quality apparatus and method which allows for the temporary adverse conditions which affect reverse osmosis membrane performance. The present invention meets this need.

SUMMARY OF THE INVENTION

The present invention includes a water quality monitoring system for a water filtering apparatus. The monitoring system comprises a first ion detecting mechanism for detecting a first ion content ($C_U$) in a first sample of water, and a second ion detecting mechanism for detecting a second ion content ($C_D$) in a second sample of water. Further, the system includes a comparator mechanism for receiving ion content data from the first and the second detecting mechanisms which determine therefrom a rejection ratio ($R_x$). This ratio ($R_x$) represents a comparison between the first ion content ($C_U$) and the second ion content ($C_D$). A storage mechanism is included for receiving and storing a sequence of rejection ratios ($R_1, \ldots R_n$) therein, each $R_x$ value being determined at a different selected time. Finally, the monitoring system includes a computation mechanism for receiving the sequence of rejection ratios ($R_1, \ldots R_n$) and for computing therefrom according to a predetermined formula a performance value (PV). This performance value (PV) is an indicator of the water filtering apparatus performance.

In another aspect of the invention, a method for monitoring the quality of water dispensed from a water purification apparatus 10 comprising the steps of determining a specific rejection ratio ($R_x$) comparing the first ion concentration ($C_U$) to the second ion concentration ($C_D$) at a selected time by the comparator means and storing each $R_x$ in the storage mechanism. The next step comprises calculating a Performance Value PV by the computer mechanism according to a predetermined equation by incorporating a sequence of rejection ratios ($R_1, \ldots R_n$) stored in the storage means, each $R_x$ being determined a different selected time. Finally, comparing the PV to a predetermined range of values corresponding to a calibrated scale in order to evaluate the overall performance of the water purification apparatus.

The present invention discounts temporary adverse environmental conditions by calculating a performance value and gauging that value against a calibrated scale to determine the overall condition of the water quality monitoring device.

BRIEF DESCRIPTION OF THE DRAWINGS

FIG. 1 is diagrammatic illustration of the point of use quality monitoring system designed in accordance with the present invention.

DETAILED DESCRIPTION OF THE PREFERRED EMBODIMENT

Reference will now be made in detail to the preferred embodiments of the invention. While the present invention has been described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

Attention is now directed to FIG. 1, where the subject water quality monitoring system, generally designated 30 is diagrammatically illustrated. In accordance with the present invention, the monitoring system 30 discounts the above-mentioned temporary adverse conditions by monitoring the performance of reverse osmosis (RO) membrane 16 over a predetermined sequence of uses or "vends" as opposed to a single vend. Thus, only a collective series of undesirable percentage differentials, in the Parts Per Million (PPM) level of dissolved solids, will determine that the RO membrane 16 is performing in a substandard fashion. Temporary fluctuations in the PPM concentration differential, between opposing sides of RO membrane 16, will not be significant enough to singularly assess the performance of the RO membrane 16. Accordingly, the quality monitoring system 30 of the present invention much more accurately determines the true condition of RO membrane 16 as compared with the previous inventions. This, of course, will be described in far greater detail below.

Generally, the percentage PPM concentration differential between the upstream fluid body 12 and the downstream fluid body 14 represents the rejection ratio (R) or the percentage of dissolved solids rejected by the RO membrane 16 during the process. In a preferred formulation, the rejection ratio $R_x$ is equivalent to:

$$R_x = (C_U - C_D)/C_U$$

where x represents a specific vend X, $C_U$=PPM concentration upstream and $C_D$=PPM concentration downstream (both of which are proportional to the measured resistivity). However, other rejection ratios may also be calculated so long as they compare the percentage of upstream and downstream solids.

In the preferred embodiment of the present invention, it has been determined that a satisfactory rejection ratio ($R_S$) of 70% is within the minimum level of acceptability for membrane performance. Accordingly, any specific rejection ratio $R_x$ falling below 70%, due to the performance of a RO membrane 16, will be deemed unacceptable. As will be discussed below, this may or may not "set-off" the indicator to "service" the RO membrane 16. Of course, it will be appreciated that $R_S$ may represent any predetermined level without departing from the true spirit and nature of the present invention.

A performance value (PV) is calculated according to a predetermined formula (discussed below) which incorporates a sequence of rejection ratios ($R_1, \ldots R_n$) as variables therein. The PV, when gauged against a calibrated scale, determines the overall condition of the RO membrane 16, or of the water purification apparatus 10. Preferably, each value of $R_x$ (i.e., ($R_1, \ldots R_n$) is determined at different selected times and only once during a single vend X. As will be described in greater detail below, in order for the water quality monitor apparatus 30 of the present invention to determine that the RO membrane 16 is sufficiently substandard, the sequence of rejection ratios ($R_1, \ldots R_n$) cumulatively falls below the predetermined acceptable range of scaled values which are measured over a period of vends. Therefore, when temporary aberrations in membrane performance occur, (i.e., when the $R_x$ value falls below $R_S$), due to temporary adverse environmental conditions, the water quality monitor 30 of the present invention will not inconvenience the user falsely alarming.

Briefly, as best viewed in FIG. 1, there is provided a reverse osmosis water purification apparatus 10 positioned between the upstream water source 12 and the downstream product water 14. A semi-permeable RO membrane 16 is positioned in a housing 18 which separates the upstream water 12 from the downstream water product 14. Thus, as mentioned above, an increase in fluid pressure on the side of the RO membrane 16 exhibiting the greater metallic ion concentration (i.e., the water supply source 12) causes the water to flow in the reverse direction, represented by arrow 20, to produce the product water 14. For illustration purposes, the reverse osmosis purification apparatus 10 is shown coupled between upstream piping 22 and downstream piping 24 which are commonly known in the field.

A first pair of electrodes 32 is disposed upstream 12 of RO membrane 16 and positioned a sufficient distance apart to make an accurate determination of the feed water resistivity, and hence, the upstream ion concentration $C_U$. Similarly, a second pair of electrodes 34 is disposed downstream 14 of RO membrane 16 to accurately determine the =downstream ion concentration $C_D$. Both the first and second pair of electrodes 32 and 34, respectively, are devices commonly known and are not claimed as novel feature of the present invention. However, it will be noted that in the preferred embodiment, the monitoring or sampling time will be limited to approximately ten milliseconds to limit plating and the electrodes caused by electrolysis. Should the electrodes become substantially coated with particles, the electrodes will be subject to mis-readings.

Water quality monitoring system 30 preferably includes a monitor housing 36 containing an array of electronic components and circuit boards (not shown), which will be described heretofore. Each of the first and second pairs of electrodes 32 and 34 are electrically coupled to a comparator circuit 38 which, in effect, measures the $C_U$ and $C_D$ of the upstream source 12 and the downstream product 14, respectively, thereby determining the specific rejection ratio $R_x$ at vend X. Preferably, each $R_x$ (or Threshold Value ($T_x$), discussed below) is stored in a memory device 42 electrically coupled to comparator circuit 38, as shown in FIG. 1. It will be noted that memory device 42 must have a capacity sufficient to store the whole sequence ($R_1, \ldots R_n$) or the like.

Furthermore, electrically intercoupled to both the comparator circuit 38 and to the memory device 42 is a main computer 40 which is formed to calculate the PV. Main computer 40 recalls the values ($R_1, \ldots R_n$) (or ($T_1, \ldots T_n$)) stored in memory device 42 and incorporates these variables in the predetermined formula. As stated above, PV corresponds to a predetermined range of scaled values which are chosen to properly evaluate the water purification apparatus' 10 performance.

Water quality monitoring system 30 preferably includes a visual three indicator display 44 which is electrically coupled to main computer 40 to indicate the current status of the purification apparatus 10 as determined by monitoring system 30. As viewed in FIG. 1, display 44 includes three indicators 46, 48 and 50 which, alone or in combination, correspond to a "good" indicator, an "alert" indicator and a "service" indicator, respectively.

A power supply 52 is shown coupled to computer 40 which provides power to quality monitoring system 30. Preferably, it is desirable to operatively power apparatus 30 through batteries. However, the present invention can easily incorporate a UL listed Class II transformer for operation on 120 VAC.

In the preferred embodiment of the present invention, when the water quality monitoring system 30 records rejection ratios R above $R_S$ (i.e., 70%), the main computer 40 will energize the "acceptable" indicator 46 to indicate to the user that the purification apparatus 10 is functioning properly. However, once the purification apparatus 10 dispenses a vend below $R_S$, the main computer 40 assigns $R_x$ a threshold value $T_x$ equal to +1 if it records a vend below Rs, signifying an "unacceptable" vend. Main computer 40 then stores $T_x$ in memory device 42. Subsequently, the $T_x$ of all consecutive future vends having an $R_x$ below $R_S$ will be stored in memory device 42 (i.e., $T_1, \ldots T_n$).

These corresponding consecutive threshold values ($T_1, \ldots T_n$) are then incorporated, as variables, in the predetermined formula calculating PV, which, preferably, is equivalent to the equation:

$$PV = (T_1 + T_2 + \ldots T_n)$$

where n represents the predetermined number of consecutive vends. As mentioned above, the summation of $T_1 + T_2 + \ldots T_n$ (i.e., PV) is gauged against a predetermined range of values corresponding to a calibrated scale chosen to properly evaluate the performance of the water purification apparatus 10.

In the preferred embodiment, the predetermined range of scaled values are set forth as such. Should the PV exceed 40 consecutive vends below $R_S$, the "alert" indicator 48 will preferably be energized. This indication 48 informs the user that product water quality has declined slightly, but that this may be due to some adverse environmental condition unrelated to the performance of the purification apparatus 10.

In the preferred form, if $R_x$ further declines below a second "alert" rejection ratio $R_{S2}$, set at a predetermined level of 60%, and the PV surpasses +100, the "servicing" indicator 48 will be energized which signifies that the RO membrane 16 requires replacement.

Moreover, in the preferred embodiment, if at any time $R_x$ declines below a third "automatic servicing" rejection ratio $R_{S3}$, predetermined to be 30%, the "servicing" indicator will automatically be energized. This indication will occur without delay, independent of the status of the PV. To further indicate the importance of this condition, which may represent a possible RO membrane 16 rupture, the main computer 40 may, in addition, flash the "servicing" indicator 50 or the like.

In accordance with the present invention, the predetermined range of scaled values are summarized in TABLE 1.

TABLE 1

| Predetermined Scale | Indicator |
| --- | --- |
| PV < +40 | "Good" Indicator |
| +40 ≦ PV ≦ +100 | "Alert" Indicator |
| PV > +100 and | "Service" Indicator |
| $R_x$ declines below $R_{S2}$ | |
| $R_x$ declines below $R_{S3}$ | "Auto-Service" Indicator |

In the preferred embodiment, if $R_{S2} \leq R_x \leq R_S$, then the "alert" indicator will be energized. Moreover, should $R_x$ exceed $R_S$, the main computer 40 will reset the PV and the storage device 42. It will be appreciated that the predetermined parameters previously mentioned may be easily modified to fit a particular need. Furthermore, the three indicators 46, 48 and 50 may be energized in numerous combination to signify a plurality of performance conditions without departing from the true spirit of the present invention.

In an alternative technique of the present invention for evaluating the RO membrane's performance, each specific rejection ratio $R_x$ will be assigned a corresponding Threshold Offset Value (T) which is factored into the predetermined formula which calculates the PV. Preferably, $R_x$ is assigned a value of −2 (i.e., T=−2) if the rejection ratio $R_x$ is above the $R_S$ value of 70%, signifying an acceptable R value, and T=1 if the R value is below the $R_S$ value, signifying an unacceptable R value. Therefore, in the sequence of rejection ratios $(R_1, \ldots R_n)$, each $R_x$ is assigned corresponding threshold offset values $(T_1, \ldots T_n)$, which, in turn, are variables in the predetermined formula.

These corresponding threshold offset values $(T_1, \ldots T_n)$ are then incorporated, as variables, in the predetermined formula calculating PV, which, preferably, is equivalent to the equation:

$$PV = (T_1 + T_2 + \ldots T_n)$$

where n represents the predetermined number of consecutive vends. Preferably, n is equal to 60 consecutive vends which is an adequate number to appropriately assess membrane performance. As mentioned above, the summation of $T_1 + T_2 + \ldots T_n$ (i.e., PV) is gauged against a predetermined range of values corresponding to a calibrated scale chosen to properly evaluate the performance of the water purification apparatus 10. In this alternative embodiment, the preferable predetermined range of scaled values are set forth in TABLE 2.

TABLE 2

| Range of PVs | Indicator |
| --- | --- |
| PV < +30 | "Good" Indicator |
| +30 ≦ PV ≦ +40 | "Alert" Indicator |
| PV > +40 | "Service" Indicator |

Accordingly, when PV is less than +30, the water quality monitor 30 signals the user that the purification apparatus 10 is determined to be functioning properly; when PV is greater than or equal to +30 and less than or equal to +40, the water quality monitor 30 "alerts" the user that the purification apparatus 10 potentially needs servicing; and when the PV is greater than +40, the water quality monitor 30 signals the user that the purification apparatus 10 requires "servicing".

Because every "acceptable" vend is worth −2 while every "unacceptable" vend is allotted +1, an "acceptable" vend is accorded twice as much weight as an "unacceptable" vend. This threshold ratio of 2:1 affords an offset for the temporary adverse condition fluctuations in the PPM found in the water supply. For example, a total of 42 "unacceptables" intermixed with 18 "acceptables" would result in a PV of +6, constituting an "acceptable" determination. In another instance, a total of 52 "unacceptables" intermixed with 8 "acceptables" would result in a PV of +36, constituting an "alert" determination. At this point, either the positive going count would continue until either the "service" condition was met, or the temporary water conditions would subside until the "acceptable" determinations begin to dominate. If the "unacceptable" rejection ratios $R_x$ continued long enough, the PV would exceed +40 thereby alerting the user that the purification apparatus 10 required "servicing" indicator.

As mentioned above, the reason for the 2:1 threshold ratio is to offset the temporary adverse conditions often found in municipal feed water supplies 12. When a batch of increased PPM feed water 12 is supplied to the water purification apparatus 10, the ratio increases until the higher PPM is monitored at the RO output. When the supplied PPM is reduced the ratio decreases across the RO even though the RO membrane 16 is performing efficiently. This condition can last for several times longer than required to deplete the RO's liquid capacity. It is for this reason that long term or consecutive reject readings are required before establishing a service required condition. It, of course, will be appreciated that the threshold ratio could be any other acceptable ratio, depending on usage or conditions. For example, the threshold ratio could be 4:1, where T=−4 for every "acceptable" vend, and where T=1 for every "unacceptable" vend.

In this alternative embodiment, main computer 40 converts the specific $R_x$ into the corresponding threshold value $(T_x)$ (i.e., T=−2 or T=1) which is then stored in memory device 42. Main computer 40 recalls the threshold values $(T_1, \ldots T_n)$ stored in memory 42, where $T_x$ is, preferably, $T_n$, and incorporates these variables in the predetermined formula to calculate the PV. This, value, as stated, is compared to the predetermined range of scaled values set forth in TABLE 1 to properly evaluate the water purification apparatus' 10 performance.

It will be appreciated that, in this alternative embodiment, the main computer 40 preferably includes a shift register so that upon vend (n+1) the main computer 40 will determine the PV by incorporating $(T_2, \ldots T_{n+1})$.

Thus, n consecutive values will always be available for the calculation of PV. The present invention, however, may just as easily only store n consecutive vends in memory device 42 and reset memory device 42 after the nth vend. Moreover, the sequence of threshold values ($T_1, \ldots T_n$) stored in memory device 42 may be reset after a predetermined period of time, such as every five days or the like, wherein a new sequence begins.

Preferably, display 44 will be mounted near the product water outlet. The three indicators 46, 48 and 50 will preferably Light Emitting Diodes (LED) of different shades. Moreover, the present invention may also include indicator combinations thereof which signify variations in the membrane condition. Further, the present invention may incorporate audio indicators as well. In contrast, the prior systems typically include only two modes of indication.

In another aspect of the present invention, the apparatus may initially delay the rejection ratio R measurement and allow the water to flow past the first and second pairs of electrodes 32 and 34 to clean them of any residue. Moreover, the PPM measurement itself will only be conducted near the beginning of each vend and require only 0.01 seconds. Thus, the calculation of the rejection ratio $R_x$ will only be measured once during vend X. However, it will be appreciated that more than one or a series of rejection ratio calculations may be made during vend X. Further, it will be appreciated that the sequence of ratios ($R_1, \ldots R_n$) is preferably a consecutive series of vends. However, the sequence could equate to every other vend or the like.

Further, as stated, by using a short measurement interval, in contrast to the prior art, plating of the electrodes will be greatly reduced. Furthermore, battery life, to activate the system, will be prolonged.

A method for monitoring the quality of water dispensed from a water purification apparatus 10 comprising the steps of determining a specific rejection ratio ($R_x$) in the ion concentration between the upstream water supply 12 and the downstream product water output 14 at a selected time by the comparator means 38 and storing each $R_x$ in the storage means 42. The next step comprises calculating a Performance Value PV by the computer means 40 according to a predetermined equation by incorporating a sequence of rejection ratios ($R_1, \ldots R_n$) stored in the storage means 42, each $R_x$ being determined a different selected. time. Finally, comparing the PV to a predetermined range of values corresponding to a calibrated scale in order to evaluate the overall performance of the water purification apparatus.

Furthermore, the method in accordance with the present invention may further include the step of energizing an indicator means connected to the computation means which is responsive to the predetermined range of values.

While the invention has been described in connection with what is presently considered to be the most practical and preferred embodiments, it is to be understood that the invention is not limited to the disclosed embodiment but, on the contrary, is intended to cover various modifications and equivalent arrangements included within the spirit and scope of the appended claims.

Therefore, persons of ordinary skill in this field are to understand that all such equivalent structures are to be included within the scope of the following claims:

What is claimed is:

1. A system for monitoring the quality of water filtered through a water filtering apparatus receiving unfiltered water and dispensing filtered water as an output, said monitoring system comprising:

first ion detecting means for detecting the ion content ($C_U$) of said unfiltered water;

second ion detecting means for detecting the ion content ($C_D$) of said filtered water;

comparator means, coupled to said first and said second ion detecting means, for determining therefrom a rejection ratio ($R_x$) proportional to ($C_D$)/($C_U$) and for quantizing said $R_x$ to a threshold value ($T_x$) when $R_x$ is less than a predetermined satisfactory rejection ratio ($R_S$), said comparator means so determining and so quantizing at least once per each dispensing of said filtered water;

storage means, coupled to said comparator means, for storing said threshold values $T_x$;

computation means, coupled to said storage means, for computing from a sequence of stored said threshold values ($T_1, \ldots T_n$) a performance value (PV) indicating quality of output filtered water dispensed by said filtering apparatus; and indicator means, coupled to said computation means, for signaling quality of said output filtered water dispensed by said filtering apparatus.

2. The quality monitoring system as defined in claim 1 further including:

indicator means for receiving said performance value (PV) and responsive to a preselected range of said performance values (PV).

3. The quality monitoring system as defined in claim 2 wherein, said indicator means comprises at least three indicators each indicator being responsive to a different preselected range of performance values (PV).

4. The quality monitoring system as defined in claim 1 wherein, said rejection ratio ($R_x$) represents ($C_U - C_D$)/$C_U$.

5. The quality monitoring system as defined in claim 1 wherein, $PV = T_1 + T_2 + \ldots T_n$, where n equals a predetermined number of consecutive dispensings of filtered water from said water filtering apparatus.

6. The quality monitoring system as defined in claim 5 further including:

indicator means for receiving said performance value (PV) and responsive to a preselected range of said performance values (PV).

7. The quality monitoring system as defined in claim 6 wherein, said indicator means comprises a first, a second and a third indicator, each indicator being responsive to a different preselected range of performance values (PV).

8. The quality monitoring system as defined in claim 7 wherein, said indicators comprises Light Emitting Diodes.

9. The quality monitoring system as defined in claim 8 wherein, said predetermined satisfactory rejection ratio ($R_S$) corresponds to 70%.

10. The quality monitoring system as defined in claim 5 wherein, said rejection ratio ($R_x$) represents ($C_U - C_D$)/$C_U$.

11. The quality monitoring system as defined in claim 5 wherein, when said $R_x \geq R_S$, said computation means causes said storage means to purge stored said threshold values and to reset said PV.

12. The quality monitoring system as defined in claim 1 wherein,
the water filtering system comprises a reverse osmosis water filtering system.

13. The quality monitoring system as defined in claim 12 wherein
the water filtering system includes an upstream unfiltered water inlet pipe, a downstream filtered water outlet pipe and a reverse osmosis filter membrane disposed therebetween.

14. The quality monitoring system as defined in claim 1 wherein,
said monitoring system is a point of use monitoring system.

15. The quality monitoring system as defined in claim 1 wherein,
said first and second ion detecting means comprise electrodes.

16. The quality monitoring system as defined in claim 1 wherein,
said sequence comprises successive measurements.

17. The quality monitoring system as defined in claim 1 wherein,
said PV is determined by a predetermined formula.

* * * * *